United States Patent [19]
Schelling et al.

[11] 3,935,271

[45] Jan. 27, 1976

[54] UNSATURATED ALIPHATIC KETONES

[75] Inventors: Hans-Peter Schelling, Oberwil; Fritz Schaub, Basel, both of Switzerland

[73] Assignee: Sandoz Ltd., Basel, Switzerland

[22] Filed: Dec. 19, 1973

[21] Appl. No.: 426,229

Related U.S. Application Data

[63] Continuation-in-part of Ser. No. 257,671, May 30, 1972, abandoned.

[30] Foreign Application Priority Data

June 2, 1971 Switzerland.................. 8036/71

[52] U.S. Cl............. 260/594; 260/586 R; 260/404; 424/331; 424/312; 260/410.9; 260/484 R; 260/465.6

[51] Int. Cl.²......................................... C07C 49/24

[58] Field of Search.................. 260/586, 594

[56] References Cited
UNITED STATES PATENTS

| | | | |
|---|---|---|---|
| 3,238,260 | 3/1966 | Pasedoch et al.............. | 260/594 |
| 3,429,970 | 2/1969 | Ruegg et al................... | 260/583 |
| 3,671,558 | 6/1972 | Siddell et al.............. | 260/410.9 R |
| 3,692,851 | 9/1972 | Henrick et al.............. | 260/561 |
| 3,697,560 | 10/1972 | Henrick et al.............. | 260/399 |
| 3,732,282 | 5/1963 | Henrick et al.............. | 260/593 R |
| 3,737,442 | 6/1973 | Baum.................... | 260/544 |
| 3,745,189 | 7/1973 | Hoffmann et al................ | 260/594 |
| 3,755,411 | 8/1973 | Henrick et al.............. | 260/594 |
| 3,783,141 | 1/1974 | Pawson et al.............. | 260/594 |
| 3,824,319 | 7/1974 | Schwarz et al.............. | 260/593 R |
| 3,826,804 | 7/1974 | Henrick et al.............. | 260/593 R |

*Primary Examiner*—James O. Thomas, Jr.
*Assistant Examiner*—James H. Reamer
*Attorney, Agent, or Firm*—Gerald D. Sharkin; Richard E. Vila

[57] ABSTRACT

The present invention concerns unsaturated ethers or thioethers of the formula:

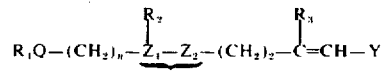

wherein $R_1$ is an aliphatic or alicyclic hydrocarbon, $R_2$ and $R_3$ are H or alkyl, Y is cyano, amido, a ketone or an acid ester,

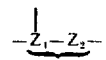

is an ether, thioether or a saturated or unsaturated c—c bond and $n$ is an integer, which exhibit insecticidal properties.

5 Claims, No Drawings

UNSATURATED ALIPHATIC KETONES

This application is a continuation-in-part of copending U.S. Ser. No. 257,671, filed May 30, 1972, now abandoned.

The present invention relates to unsaturated ethers or thioethers.

The present invention provides compounds of formula I,

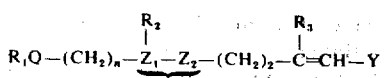     I wherein

R$_1$ is alkyl of 1 to 10 carbon atoms; alkenyl of 3 to 10 carbon atoms; alkynyl of 3 to 10 carbon atoms; cycloalkyl of 3 to 6 carbon atoms; cycloalkyl of 3 to 6 carbon atoms substituted by alkyl of 1 to 4 carbon atoms; cycloalkenyl of 5 to 7 carbon atoms; cycloalkenyl of 5 to 7 carbon atoms substituted by alkyl of 1 to 4 carbon atoms; cycloalkyl(of 3 to 6 carbon atoms)alkyl (of 1 to 4 carbon atoms); cycloalkyl(of 3 to 6 carbon atoms)alkyl (of 1 to 4 carbon atoms) ring substituted by alkyl of 1 to 4 carbon atoms; cycloalkenyl(of 5 to 7 carbon atoms)alkyl (of 1 to 4 carbon atoms); or cycloalkenyl(of 5 to 7 carbon atoms)alkyl (of 1 to 4 carbon atoms) ring substituted by alkyl of 1 to 4 carbon atoms;

R$_2$ and R$_3$, which are the same or different, are each hydrogen or alkyl of 1 to 4 carbon atoms, Y is cyano;
 —CONR$_4$R$_5$ wherein R$_4$ and R$_5$, which are the same or different, are each hydrogen or alkyl of 1 to 4 carbon atoms, or R$_4$ and R$_5$ together with the nitrogen atom constitute a 5 or 6 membered heterocycle containing either one ring nitrogen atom or one ring nitrogen atom and one ring oxygen atom, e.g. pyrrolidine, piperidine or morpholine;
 —COOR$_6$ wherein R$_6$ is alkyl of 1 to 5 carbon atoms; or COR$_7$ wherein R$_7$ is alkyl of 1 to 5 carbon atoms;

Q is oxygen or sulphur;

$-\overset{|}{Z_1}-\overset{|}{Z_2}-$ is $-\overset{|}{C}H-O-$, $-\overset{|}{C}H-S-$, $-\overset{|}{C}H-CH_2-$ or $-\overset{|}{C}=CH-$; and n is an integer 1, 2 or 3.

When any of R$_1$, R$_2$, R$_3$, R$_4$, R$_5$, R$_6$ and R$_7$ are aliphatic groups of more than 2 carbon atoms, they may be straight or branched chain.

The present invention also provides processes for the production of a compound of formula I which comprises a. reacting a compound of formula II,

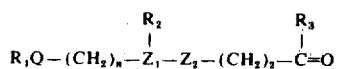     II wherein

R$_1$, R$_2$, R$_3$, Q,

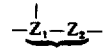

and n are as defined above
with a compound of formula III,

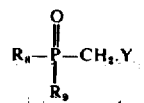     III wherein

Y is as defined above and

R$_8$ and R$_9$, which are the same or different, are each phenyl, alkoxy of 1 to 4 carbon atoms or aryloxy (e.g. phenyloxy or toluyloxy), in the presence of a strong base (i.e. under Wittig-Horner conditions - Houben-Weyl, Methoden der Organischen Chemie, Ed. E. Müller, Vol. V/1c page 603 [1970]) or b. reacting a compound of formula II with a compound of formula IV,

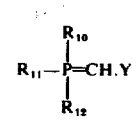     IV wherein

Y is as defined above and

R$_{10}$, R$_{11}$ and R$_{12}$ are each aryl (e.g. phenyl, alkylphenyl, such as meta methyl-, ethyl-, n-propoyl- or i-propyl- substituted phenyl, alkoxyphenyl, such as para methoxy-, ethoxy-, n-propoxy- or i-propoxy-substituted phenyl, or chloro-or bromo-substituted phenyl, such as para chloro-substituted phenyl) or dialkylamino of 2 to 8 carbon atoms or c. reacting a compound of formula V,

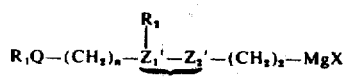     V wherein

R$_1$, R$_2$, Q and n are as defined above, $-\overset{|}{Z_1'}-\overset{|}{Z_2'}-$ is $-\overset{|}{C}H-CH_2-$ or $-\overset{|}{C}=CH-$, and X is chlorine or bromine, with a compound of formula VI,

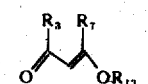     VI wherein

R$_3$ and R$_7$ are as defined above and

R$_{13}$ is alkyl of 1 to 4 carbon atoms, with subsequent acid hydrolysis and dehydration, to produce a compound of formula Ia,

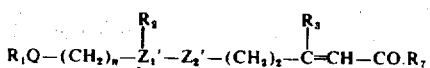     Ia wherein $R_1, R_2, R_3, R_7, Q,$

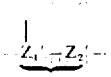

and n are as defined above or d. reacting a compound of formula Ib

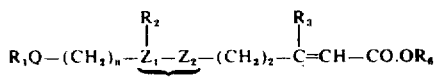    Ib wherein $R_1, R_2, R_3, R_6, Q,$

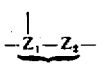

and n are as defined above
with a compound of formula VII, $MNR_4R_5$      VII wherein $R_4$ and $R_5$ are as defind above and
M is hydrogen, lithium or MgBr,
to produce a compound of formula Ic

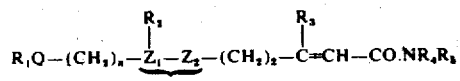    Ic wherein $R_1, R_2, R_3, R_4, R_5, Q,$

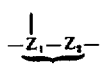

and n are as defined above.

Process a) may, for example, be effected as follows, viz:

A strong base such as sodium hydride, in for example, an ether such as 1,2-dimethoxyethane, tetrahydrofurane, diethylether or dioxane, or an amide such as dimethylformamide, as a solvent or as suspension medium, or potassium tert.butoxide in for example, benzene, toluene or tetrahydrofurane as a solvent or a suspension medium, or a sodium alcoholate in for example dimethylformamide as a solvent or a suspension medium, may be added to a compound of formula VII, preferably while stirring and conveniently at room temperature. The mixture may be stirred for a period of about 8 hours and a compound of formula II then added in a solvent, conveninetly that employed for the strong base. The mixture may be stirred for a period of about 20 hours conveniently at room temperature after which time water may be added with cooling. Working up may be effected in conventional manner e.g. by extraction with benzene.

Process b) may, for example, be effected as follows viz:

A compound of formula II, in a solvent such as an ether, for example, dioxane or tetrahydrofurane, may be reacted with a compound of formula IV, preferably at an elevated temperature, for example, at reflux temperature, conveniently over a prolonged period, for example about 24 hours. In some circumstances, the compound of formula IV may conveniently be produced in situ. Working up may be effected in conventional manner.

Process c) may, for example, be effected as follows viz:

A compound of formula VI may be added to a compound of formula V in a solvent such as an ether, for example diethyl ether or tetrahydrofurane. After a period of between about 2 and 6 hours, conveniently at room temperature, a dilute mineral acid such as dilute hydrochloric acid or dilute sulphuric acid may be added to the mixture, the resulting magnesium salt and enol ether being hydrolysed with subsequent elimination of water. Working up may be effected in conventional manner.

Process d) may, for example, be effected as follows viz:

A compound of formula VII in a solvent such as absolute ether may be added to a compound of formula Ib in the same solvent conveniently with stirring and at room temperature. The reaction may be allowed to proceed over a prolonged period e.g. up to 12 hours. Working up is effected in manner known per se.

The compound of formula II employed as starting material in processes a) and b) above may be produced as follows viz:

a'. the compounds of formula IIa,

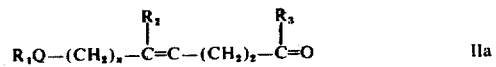    IIa wherein $R_1, R_2, R_3, Q$ and n are as defined above
may be produced by reacting a compound of formula VIII,

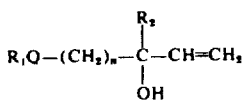    VIII wherein $R_1, R_2, Q$ and n are as defined above
with a compound of formula XIII,

    XIII wherein $R_3$ is as defined above and
$R_{14}$ is methyl or ethyl,
in manner known per se.

b'. The compounds of formula IIb

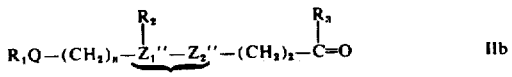    IIb wherein $R_1, R_2, R_3, Q$ and n are as defined above and

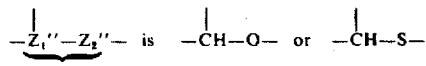 is —CH—O— or —CH—S— may be produced by etherifying a compound of formula IX,

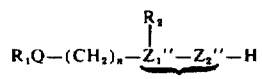 IX wherein
R₁, R₂, Q,

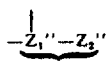

and $n$ are as defined above,
with a compound of formula X,

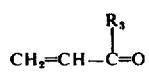 X wherein
R₃ is as defined above,
in manner known per se.

c'. The compounds of formula IIc,

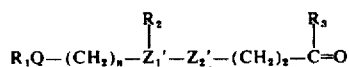 IIc wherein
R₁, R₂, R₃, Q,

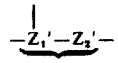

and $n$ are as defined above,
may be produced by reacting a compound of formula XI,

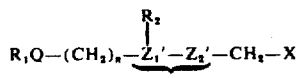 XI wherein
R₁, R₂, Q,

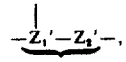, n and X are as defined above,
with a compound of formula XIII with subsequent hydrolysis and decarboxylation, in manner known per se.

d'. The compounds of formula IId,

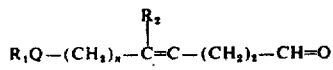 IId wherein
R₁, R₂, Q and n are as defined above,
may be produced by reacting a compound of formula VIII, with an alkylvinyl ether of 3 to 7 carbon atoms, in the presence of mercuric acetate. The reaction may be effected at elevated temperature and over a prolonged period e.g. 4 days, with subsequent rearrangement while heating at a temperature of, for example, 160°–190°C, over a period of, for example, 1 to 2 hours.

e'. The compounds of formula IIe

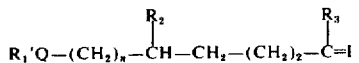 IIe wherein
R₁' is alkyl of 1 to 10 carbon atoms; cycloalkyl of 3 to 6 carbon atoms; cycloalkyl of 3 to 6 carbon atoms substituted by alkyl of 1 to 4 carbon atoms; cycloalkyl (of 3 to 6 carbon atoms)alkylene(of 1 to 4 carbon atoms); or cycloalkyl(of 3 to 6 carbon atoms)alkylene(of 1 to 4 carbon atoms) ring substituted by alkyl of 1 to 4 carbon atoms; and
R₂, R₃, Q and n are as defined above,
may be produced by catalytic hydrogenation of a compound of formula IIf

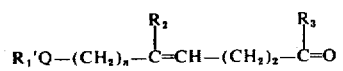 IIf wherein
R₁', R₂, R₃, Q and $n$ are as defined above,
in conventional manner.

The compounds of formula VIII may, for example, be produced by reacting a compound of formula XII,

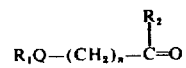 XII wherein
R₁, R₂, Q and $n$ are as defined above,
with vinyl magnesium chloride or bromide.

The compounds of formulae III, IV, V, VI, VII, IX, X, XI, XII and XIII are either known or may be produced in analogous manner to the process for producing the known compounds.

The compounds of formula I are colourless oils. They may be characterised and purified in the normal manner e.g. purification by distillation or chromatography.

The compounds of formula I are useful as insecticides as indicated in the following tests by an inhibiting effect on the development of the insects *Dysdercus Fasciatus* (Egyptian cotton worm) and *Prodenia littura* (cotton stainer) from one development stage thereof to the next, to result either in death, reduced oviposition or inhibition of copulation, viz:

TEST 1

Insecticidal effect on *Dysdercus fasciatus* larvae
(Egyptian cotton worm)

Filter paper is impregnated with a solution of a compound of formula I viz:

a) methyl-[9-sec.butoxy-3,7-dimethyl]2,6-nonadienoate,
b) 9-sec.butoxy-3,7-dimethyl-2,6-nonadiene-1-nitrile,
c) methyl-[9-isopropoxy-3,7-dimethyl]2,6-nonadienoate,
d) 10-isopropoxy-8-methyl-3,7-decadien-2-one, and
e) 10-isopropoxy-4,8-dimethyl-3,7-decadien-2-one, at a concentration of 0.1 mg/cm².

A box made from polystyrene (200 × 100 × 85 mm) is coated with the filter paper treated in this way. A folded filter paper, which is also impregnated, is covered with about 30 dysdercus larvae of the 4th larval stage and placed into the box. Pounded cotton seeds as food and a drinking-vessel are placed into it. The mortality is determined after 10 days. Substantial mortality is observed.

TEST 2

Effect on the development of *Prodenia*-littura larvae (cotton strainer) into adults Filter paper is impregnated with a solution of a compound of formula I viz:

a) methyl-[9-sec.butoxy-3,7-dimethyl]2,6-dienoate
b) methyl-[9-isopropoxy-3,7-dimethyl]2,6-nonadienoate,
c) 10-isopropoxy-8-methyl-3,7-decadien-2-one, and
d) 10-isopropoxy-4,8-dimethyl-3,7-decadien-2-one, at a concentration of 0.1 mg/cm² Partitions, having a size of 3.5 × 5.5 cm, of a plastic box are coated with the filter paper treated in this way. One Prodenia caterpillar in the third to fourth larval stage is placed into each partition and a piece of artificial medium is given as food. The insects are kept at 25°. The number of the adults which have developed normally after 21 days is determined. The rate of development is found to be substantially checked.

In addition, the compounds of formula I are further useful as insecticides because they exhibit low toxicity towards warm blooded animals.

It is to be understood that the term "insects" as used herein is used in a broad sense and may include not only the class Insecta, but classes of similar or related organisms e.g. spider mites. The term "insecticide" and "insecticidal" as used herein should be construed accordingly.

For the abovementioned use, the amount applied to a locus to be treated will of course vary depending on the compound employed, the mode of application, ambient conditions, and the insects to be combated. However, with regard to plant protection, satisfactory results are obtained when applied to a plant locus in an amoount of between 1 and 4 kg/hectare, the application being repeated as required.

The compounds may be applied to the locus with conventional applicator equipment and by conventional methods e.g. strewing, spraying and dusting.

Compositions may comprise a compound of formula I in admixture with insecticide carriers, diluents and/or adjuvants in solid or liquid form e.g. spraying and dusting powders, granulates, liquid sprays and aerosols.

Solid forms may include diluents and carriers such as diatomaceous earth, bentonite and pumice. Adjuvants e.g. surfactants such as wetting and dispersing agents and adhesive agents, e.g. cellulose derivatives, may also be included in the case of wettable powders to be applied as a water suspension. Granulates are produced by coating or impregnating granular carrier materials such as pumice, limestone, attapulgite and koalinite with the compounds.

Liquid forms may include non-phytotoxic diluents and carriers such as alcohols, glycolic ethers, aliphatic and aromatic hydrocarbons e.g. xylene, alkyl napthalenes and other petroleum distillates. Adjuvants such as surface active agents, e.g. wetting and emulsifying agents such as polyglycol ethers formed by the reaction of an alkylene oxide with high molecular weight alcohols, mercaptans or alkyl phenols, may be included in emulsion concentrate forms. Appropriate organic solvents e.g. ketones, aromatic optionally halogenated hydrocarbons and mineral oils may also be included as solvent aids.

Aside from the abovementioned carriers, diluents and adjuvants, adjuvants such as U. V. stabilizing agents, desactivators (for solid forms with carriers having an active surface), agents for improving adhesiveness to surfaces treated, anticorrosives, defoaming agents and pigments may also be included.

Concentrate forms of composition generally contain between 2 and 90 percent, preferably between 5 and 50 percent, by weight of active compound.

Application forms of composition generally contain between 0.01 and 20 percent and preferably between 0.1 and 20 percent, by weight of active compound.

Examples of concentrate forms of composition will now be described.

a. Emulsifiable Concentrate 25 parts by weight of a compound of formula I are mixed with 25 parts by weight of isooctylphenyldecaglycol ether and 50 parts by weight of xylene, whereby a clear solution is obtained which may be readily emulsified in water. The concentrate may be diluted with water to the desired concentration.

b. Emulsifiable Concentrate 25 parts by weight of a compound of formula I are mixed with 30 parts by weight of isooctylphenyloctaglycol ether and 45 parts by weight of a petroleum fraction having a B.P. of 210°–280° ($D_{20}$ : 0.92). The concentrate may be diluted with water to the desired concentration.

c. Emulsifiable Concentrate 50 parts by weight of a compound of formula I are mixed with 50 parts by weight of isooctylphenyloctaglycol ether. A clear concentrate is obtained which may be readily emulsified in water and which may be diluted with water to the desired concentration.

The preferred compounds of formula I are generally those compound wherein
 $R_1$ is alkyl of 1 to 6 carbon atoms,
 $R_2$ and $R_3$, which are the same or different, are each hydrogen or alkyl of 1 to 4 carbon atoms,
 Q is oxygen, $-Z_1-Z_2-$ is $-CH-O-$, $-CH-CH_2-$ or $-C=CH-$, y is cyano; $COOR_6$ wherein $R_6$ is alkyl of 1 to 5 carbon atoms; or $COR_7$ wherein $R_7$ is alkyl of 1 to 5 carbon atoms and n is an integer 1, 2 or 3.

Specific preferred compounds are
methyl-[9-sec.butoxy-3,7-dimethyl]2,6-nonadienoate,
9-sec.butoxy-3,7-dimethyl-2,6-nonadiene-1-nitrile and methyl-[9-isopropoxy-3,7-diemthyl]2,6-nonadienoate.

The following Examples illustrate the production of the compounds of formula I, but in no way limit the invention. The temperatures are indicated in degrees Centigrade. Where concentration is indicated as a %, this is % by weight. Where pressure is indicated in mm this is mm/Hg.

EXAMPLE 1

Methyl-[9-sec.butoxy-3,7-dimethyl]-2,6-nonadienoate [process a)]

1.31 g (0.03 mol) of a 55 % sodium hydride emulsion in mineral oil are washed with hexane and suspended in 45 cc of 1,2-dimethoxy ethane in an atmosphere of nitrogen. 6.3 g (0.03 mol) of methyl-(O,O-diethylphosphono)acetic acid are added at 20°–25° during the course of 1 hour and while stirring. After 8 hours 4.24 g (0.02 mol) of 8-sec.butoxy-6-methyl-5-octen-2-one in 6 cc of 1,2-dimethoxy ethane are added dropwise and the mixture is stirred at 20°–25° for 20 hours. Working up is effected by the dropwise addition of 100 c of water with cooling. The organic phase is extracted with benzene; the benzene extract is concentrated by evaporation to 60 cc, is filtered through 30 g of aluminium oxide (activity II) and the filtrate is evaporated. The residue may be purified on silica gel by chromatography [eluant hexane/acetic ester (9:1)], whereby a cis/trans isomeric mixture of methyl-[9-sec.-butoxy-3,7-dimethyl]-2,6-nonadienoate is obtained. $n_D^{20}$ = 1.4678

Analysis: $C_{16}H_{28}O_3$: Molecular weight 268.4 Calc.: C, 71.6 %; H, 10.5 %; O, 17.9 %. Found: C, 71.9 %; H, 10.2 %; O, 18.3 %.

EXAMPLE 2

Methyl-[9 -isopropoxy 3,7-dimethyl]-2,6-nonadienoate [process a)]

The above compound is produced in analogous manner to that described in Example 1, but using 8-isopropoxy-6-methyl-5-octen-2-one in place of 8-sec.-butoxy-6-methyl-5-octen-2-one.

$n_D^{20}$ = 1.4691

Analysis: $C_{15}H_{26}O_3$: Molecular weight: 254.4. Calc.: C, 70.8 %; H, 10.3 %. Found: C, 71.2 %; H, 10.4 %.

EXAMPLE 3

Methyl-[5-(4-isopropoxy-2-butyloxy)-3-methyl]-2-pentenoate [process a)]

The above compound is produced in analogous manner to that described in Example 1, but using 4-(4-isopropoxy-2-butyloxy)-2-butanone in place of 8-sec.-butoxy-6-methyl-5-octen-2-one.

$n_D^{20}$ = 1.4521

Analysis: $C_{14}H_{26}O_4$: Molecular weight: 258.4. Calc.: C, 65.1 %; H, 10.1 %. Found: C, 65.4 %; H, 10.4 %.

EXAMPLE 4

Ethyl-[10-isopropoxy-3-methyl]-2-decenoate [process a)]

The above compound is produced in analogous manner to that described in Example 1, but using 9-isopropoxy-2-nonanone in place of 8-sec.butoxy-6-methyl-5-octen-2-one and ethyl-(O,O-diethyl-phosphono)-acetic acid in place of methyl-(O,O-diethyl-phosphon)-acetic acid.

$n_D^{20}$ = 1.4527

Analysis: $C_{16}H_{30}O_3$: Molecular weight: 270.4. Calc.: C, 71.1 %; H 11.2 %; O, 17.7 %. Found: C, 71.6 %; H, 11.2 %; O, 17.7 %.

EXAMPLE 5

Methyl-[5-(1-sec.butoxy-3-pentyloxy)-3-methyl]-2-pentenoate [process a)]

The above compound is synthesized in analogous manner to that described in Example 1. The 4-(1-sec-butoxy-3-pentyloxy)-2-butanone used as starting material in place of 8-sec.butoxy-6-methyl-5-octen-2-one is produced in accordance with Example 14 below.

$n_D^{20}$ = 1.4527

Analysis: $C_{16}H_{30}O_4$: Molecular weight: 286.4. Calc.: C, 67.1 %; H, 10.6 %. Found: C, 68.0 %; H, 10.7 %.

EXAMPLE 6

Ethyl-[9-isopropoxy-3,7-dimethyl]-2-nonenoate [process a)]

The above compound is produced in analogous manner to that described in Example 1, but using ethyl-(O,O-diethylphosphono)-acetic acid in place of methyl-(O,O-diethylphosphono)-acetic acid and 8-isopropoxy-6-methyl-2-octanone in place of 8-sec.butoxy-6-methyl-5-octen-2-one.

$n_D^{20}$ = 1.4532

Analysis: $C_{16}H_{30}O_3$: Molecular weight: 270.4. Calc.: C, 71.1 %; H, 11.2 %; O 17.7 %. Found: C, 70.7 %; H, 10.8 %; O, 18.4 %.

EXAMPLE 7

10-Isopropoxy-8-methyl-3,7-decadien-2-one [process b)]

1.84 g (0.01 mol) of 7-isopropoxy-5-methyl-4-heptenal and 3.18 g (0.01 mol) of triphenyl-acetyl methylene phosphorane (M.P. 199.5°–201.5°), produced in accordance with D. B. Denney and S. T. Ross, J. Org. Chem. 27, 998 [1962], are boiled together under reflux for 24 hours in 30 cc of tetrahydrofurane. The tetrahydrofurane is then evaporated, the residue is taken up in hexane, and filtered off from the insoluble part and the hexane is evaporated. The oily residue may be purified by chromatography on silica gel with benzene/methanol 96:4. Pure 10-isopropoxy-8-methyl-3,7-decadien-2-one is obtained.

$n_D^{20}$ = 1.4716

Analysis: $C_{14}H_{24}O_2$: Molecular weight: 224.3. Calc.: C, 75.0 %; H, 10.8 %. Found: C, 75.1 %; H, 10.9 %.

EXAMPLE 8

9-sec.Butoxy-3,7-dimethyl-2,6-nonadiene-1-nitrile [process a)]

To a suspension of 0.48 g (0.01 mol) of 50 % sodium hydride dispersion in 25 cc of absolute 1,2-dimethoxy ethane there is added dropwise at 25° 1.77 g (0.01 mol) of 0,0-diethylcyano methyl phosphonate. After stirring for 2 hours at 25°, 2.12 g (0.01 mol) of 8-sec.butoxy-6-methyl-5-octen-2-one are added and the mixture is stirred over the course of 18 hours at 25°. 50 cc of ether and 150 cc of water are subsequently added and the aqueous phase is extracted with ether. The ether extract is washed with saturated salt solution, dried with sodium sulphate and evaporated. The residue is chromatographed on silica gel with chloroform as eluant, whereby the 9-sec.butoxy-3,7-dimethyl-2,6-nonadiene- 1-nitrile is obtained as colourless oil consisting of about equal parts of the cis and trans isomers.

$n_D^{20} = 1.4720$

Analysis: $C_{15}H_{25}NO$: Molecular weight: 235.4. Calc.: C, 76.5 %; H, 10.7 %; N, 6.0 %. Found: C, 77.0 %; H, 10.9 %; N, 5.6 %;

EXAMPLE 9

10-Isopropoxy-4,8-dimethyl-3,7-decadien-2-one [process c)]

To the Grignard reagent, produced from 0.46 g (0.019 mol) of magnesium and 4.5 g (0.019 mol) of 1-bromo-6-isopropoxy-4-methyl-3-hexene in 60 cc of absolute ether, there is added dropwise at 5° over the course of 15 minutes and while stirring, a solution of 2.45 g (0.019 mol) of 4-ethoxy-3-penten-2-one. After stirring for 4 hours at 20° the mixture is poured on ice cold 2N sulphuric acid and is extracted with ether. The ether extract is washed with saturated sodium bicarbonate solution, water and saturated salt solution, then dried over sodium sulphate and evaporated. After chromatography of the residue on 200 g of silica gel with hexane/ethyl acetate (9:1) as eluant, 10-isopropoxy-4,8-dimethyl-3,7-decadien-2-one is obtained as a colourless oil.

$n_D^{20} = 1.4726$

Analysis: $C_{15}H_{26}O_2$: Molecular weight: 238.4. Calc.: C, 75.5%; H, 10.9 %. Found: C, 74.6 %; H, 10.9 %.

EXAMPLE 10

N,N-diethyl-[9-isopropoxy-3,7-dimethyl]-2-nonenoic acid amide [process d)]

1.46 g (0.02 mol) of diethylamine in 10 ml of absolute ether are added to a 6 ml of a 20 % solution of butyllithium in hexane in a nitrogen atmosphere with stirring at −10°. The reaction mixture is then stirred for 1 hour at 20° when it is added to a solution of 5.4 g (0.02 mol) of ethyl-[9-isopropoxy-3,7-dimethyl]-2-nonenoate (produced in accordance with Example 6) in 10 ml of absolute ether.

After 4 hours at 25°, 10 ml of water, followed by 10 ml of 0.2 % sodium chloride solution, are added to the reaction mixture. The aqueous phase is extracted with ether, the ether extract is washed with water, dried with sodium sulphate and the ether evaporated off.

After chromatography on a silica gel column with hexane/acetic acid ester (9:1) as eluant, N,N-diethyl-[9-isopropoxy-3,7-dimethyl]-2-nonenonic acid amide, as a colourless oil is obtained.

Analysis: $C_{18}H_{35}NO_2$: Molecular weight: 297.4. Calc.: C, 72.7 %; H, 11.8 %; N, 4.7 %. Found: C, 72.1 %; H, 11.5 %; N, 4.4 %.

The following compounds of formula I may be produced by an analogous process to that described in the preceding Examples. The significances for $R_1$, $R_2$, $R_3$, Q,

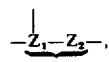

Y and n, and the preceding Example according to which the compounds may be produced are set out set below:

| $R_1$ | $R_2$ | $R_3$ | Q | $-Z_1-Z_2-$ | Y | n | Example |
|---|---|---|---|---|---|---|---|
| n-decyl | n-butyl | methyl | S | —CH—S— | n-pentoxy-carbonyl | 1 | 1 |
| ethyl | methyl | sec.butyl | O | —C=CH— | n-pentyl-carbonyl | 1 | 9 |
| 9-decenyl | methyl | methyl | O | —C=CH— | aminocarbonyl | 1 | 1 |
| propargyl | methyl | methyl | O | —CH—O— | di-n-butylaminocarbonyl | 1 | 1 |
| 9-decinyl | methyl | methyl | S | —CH—S— | pyrrolidinocarbonyl | 1 | 1 |
| cyclopropanyl | methyl | methyl | S | —CH—S— | piperidinocarbonyl | 1 | 1 |
| 2-methylcyclopropanyl | methyl | methyl | S | —CH—S— | morpholinocarbonyl | 1 | 1 |
| 2-tert.butylcyclopropanyl | methyl | methyl | O | —CH—O— | pyrrolidinocarbonyl | 2 | 1 |
| 4(2-tert.butylcyclopropanyl)-n-butyl | methyl | methyl | O | —CH—O— | pyrrolidinocarbonyl | 2 | 1 |
| cyclopentenyl | methyl | methyl | O | —CH—O— | piperidinocarbonyl | 2 | 1 |
| cyclohexyl | methyl | methyl | O | —C=CH— | methoxycarbonyl | 2 | 1 |
| 4-methylcyclohexyl | methyl | methyl | O | —C=CH— | methoxycarbonyl | 2 | 1 |
| 4-n-butylcyclohexyl | methyl | methyl | O | —C=CH— | methoxycarbonyl | 2 | 1 |
| 4(4-n-butylcyclohexyl)-n-butyl | | | | | methoxycarbonyl | 2 | 1 |
| 2-cyclohexenyl | methyl | methyl | O | —C=CH— | methoxycarbonyl | 2 | 1 |
| 4-methyl-3-cyclohexenyl | methyl | methyl | O | —C=CH— | methoxycarbonyl | 2 | 1 |
| 4-n-butyl-3-cyclohexenyl | methyl | methyl | O | —C=CH— | methoxycarbonyl | 2 | 1 |
| 4(4-n-butyl-3-cyclohexenyl)-n-butyl | methyl | methyl | O | —C=CH— | methoxycarbonyl | 2 | 1 |

-continued

| R₁ | R₂ | R₃ | Q | $-Z_1-Z_2-$ | Y | n | Example |
|---|---|---|---|---|---|---|---|
| n-decyl | n-butyl | hydrogen | O | —C(|)=CH— | n-pentyl carbonyl | 1 | 9 |
| n-decyl | hydrogen | n-butyl | O | —C(|)=CH— | n-pentyl carbonyl | 1 | 9 |
| ethyl | methyl | sec.butyl | O | —C(|)=CH— | n-pentyl carbonyl | 1 | 9 |
| 9-decenyl | methyl | methyl | O | —C(|)=CH— | methyl carbonyl | 1 | 9 |
| propargyl | methyl | methyl | O | —C(|)=CH— | ethyl carbonyl | 1 | 9 |
| 9-decinyl | methyl | methyl | O | —C(|)=CH— | n-propyl carbonyl | 1 | 9 |
| cyclopropanyl | methyl | methyl | O | —C(|)=CH— | n-butyl carbonyl | 1 | 9 |
| 2-methylcyclopropanyl | methyl | methyl | O | —C(|)=CH— | methyl carbonyl | 1 | 9 |
| 2-tert.butylcyclopropanyl | methyl | methyl | O | —C(|)=CH— | methyl carbonyl | 2 | 9 |
| 4(2-tert.butylcyclopropanyl)-n-butyl | methyl | methyl | O | —C(|)=CH— | methyl carbonyl | 2 | 9 |
| cyclopentenyl | methyl | methyl | O | —C(|)=CH— | methyl carbonyl | 2 | 9 |
| cyclohexyl | methyl | methyl | O | —C(|)=CH— | methyl carbonyl | 2 | 9 |
| 4-methylcyclohexyl | methyl | methyl | O | —C(|)=CH— | methyl carbonyl | 2 | 9 |
| 4-n-butylcyclohexyl | methyl | methyl | O | —C(|)=CH— | methyl carbonyl | 2 | 9 |
| 4(4-n-butylcyclohexyl)-n-butyl | methyl | methyl | O | —C(|)=CH— | methyl carbonyl | 2 | 9 |
| 2-cyclohexenyl | methyl | methyl | O | —C(|)=CH— | methyl carbonyl | 2 | 9 |
| 4-methyl-3-cyclohexenyl | methyl | methyl | O | —C(|)=CH— | methyl carbonyl | 2 | 9 |
| 4-n-butyl-3-cyclohexenyl | methyl | methyl | O | —C(|)=CH— | methyl carbonyl | 2 | 9 |
| 4(4-n-butyl-3-cyclohexenyl)-n-butyl | methyl | methyl | O | —C(|)=CH— | methyl carbonyl | 2 | 9 |
| n-decyl | n-butyl | hydrogen | O | —CH(|)—CH₂— | n-pentyl carbonyl | 1 | 9 |
| n-decyl | hydrogen | n-butyl | O | —CH(|)—CH₂— | n-pentyl carbonyl | 1 | 9 |
| ethyl | methyl | sec.butyl | O | —CH(|)—CH₂— | n-pentyl carbonyl | 1 | 9 |
| 9-decenyl | methyl | methyl | O | —CH(|)—CH₂— | methyl carbonyl | 1 | 9 |
| propargyl | methyl | methyl | O | —CH(|)—CH₂— | ethyl carbonyl | 1 | 9 |
| 9-decinyl | methyl | methyl | O | —CH(|)—CH₂— | n-propyl carbonyl | 1 | 9 |
| cyclopropanyl | methyl | methyl | O | —CH(|)—CH₂ | n-butyl carbonyl | 1 | 9 |
| 2-methylcyclopropanyl | methyl | methyl | O | —CH(|)—CH₂— | methyl carbonyl | 1 | 9 |
| 2-tert.butylcyclopropanyl | methyl | methyl | O | —CH(|)—CH₂— | methyl carbonyl | 2 | 9 |
| n-decyl | n-butyl | hydrogen | S | —C(|)=CH— | n-pentyl carbonyl | 1 | 9 |
| n-decyl | hydrogen | n-butyl | S | —C(|)=CH— | n-pentyl carbonyl | 1 | 9 |
| ethyl | methyl | sec.butyl | S | —C(|)=CH— | n-pentyl carbonyl | 1 | 9 |
| 9-decenyl | methyl | methyl | S | —C(|)=CH— | methyl carbonyl | 1 | 9 |
| propargyl | methyl | methyl | S | —C(|)=CH— | ethyl carbonyl | 1 | 9 |
| 9-decinyl | methyl | methyl | S | —C(|)=CH— | n-propyl carbonyl | 1 | 9 |
| cyclopropanyl | methyl | methyl | S | —C(|)=CH— | n-butyl carbonyl | 1 | 9 |
| 2-methylcyclopropanyl | methyl | methyl | S | —C(|)=CH— | methyl carbonyl | 1 | 9 |
| 2-tert.butylcyclopropanyl | methyl | methyl | S | —C(|)=CH— | methyl carbonyl | 2 | 9 |
| n-decyl | n-butyl | hydrogen | S | —CH(|)—CH₂— | n-pentyl carbonyl | 1 | 9 |
| n-decyl | hydrogen | n-butyl | S | —CH(|)—CH₂— | n-pentyl carbonyl | 1 | 9 |
| ethyl | methyl | sec.butyl | S | —CH(|)—CH₂— | n-pentyl carbonyl | 1 | 9 |
| 9-decenyl | methyl | methyl | S | —CH(|)—CH₂— | methyl carbonyl | 1 | 9 |
| propargyl | methyl | methyl | S | —CH(|)—CH₂— | ethyl carbonyl | 1 | 9 |
| 9-decinyl | methyl | methyl | S | —CH(|)—CH₂— | n-propyl carbonyl | 1 | 9 |
| cyclopropanyl | methyl | methyl | S | —CH(|)—CH₂ | n-butyl carbonyl | 1 | 9 |
| 2-methylcyclopropanyl | | | | | methyl | | |

| $R_1$ | $R_2$ | $R_3$ | Q | $-Z_1-Z_2-$ | Y | n | Example |
|---|---|---|---|---|---|---|---|
| panyl | methyl | methyl | S | $-\overset{\mid}{C}H-CH_2-$ | carbonyl | 1 | 9 |
| 2-tert.butylcyclopropanyl | methyl | methyl | S | $-\overset{\mid}{C}H-CH_2-$ | methyl carbonyl | 2 | 9 |

STARTING MATERIALS

Compounds of formula II

The following Examples 11 to 20 are representative of the processes for the production of the compounds of formula II employed as starting material in processes a) and b).

EXAMPLE 11

8-sec.Butoxy-6-methyl-5-octen-2-one 8.06 g (0.05 mol) of 5-sec.butoxy-3-methyl-1-penten-3-ol and 11.6 g (0.1 mol) of acetoacetic acid methyl ester are heated to 135° in a round bottom flask with a fractionating column and in an atmosphere of nitrogen. The methyl alcohol which is liberated during the reaction distils into the receiver. After 1 hour the reaction temperature is increased to 182°–185° at which temperature the reaction mixture is maintained for 5 hours. After cooling, the reaction mixture is fractionally distilled at reduced pressure. A cis/trans mixture of 8-sec.butoxy-6-methyl-5-octen-2-one is obtained. B.P. 105°–109°/0.8 mm.

$n_D^{20} = 1.4534$

Analysis: $C_{13}H_{24}O_2$: Molecular weight: 212.3. Calc.: C, 73.5 %; H, 11.4 %. Found: C, 73.4 %; H, 10.9 %.

EXAMPLE 12

8-Isopropoxy-6-methyl-5-octen-2-one

The compound is produced in analogous manner to that described in Example 11, but using 5-isopropoxy-3-methyl-1-penten-3-ol in place of 5-sec.butoxy-3-methyl-1-penten-3-ol. B.P. 117°–119°/8 mm.

$n_D^{20} = 1.4473$

Analysis: $C_{12}H_{22}O_2$: Molecular weight: 198.3. Calc.: C, 72.7 %; H, 11.2 %. Found: C, 72.4 %; H, 11.0 %.

EXAMPLE 13

8-Isopropylthio-6-methyl-5-octen-2-one

The above compound is produced in analogous manner to that described in Example 11, except that 5-isopropylthio-3-methyl-1-penten-3-ol is used in place of 5-sec.butoxy-3-methyl-1-penten-3-ol and that the reaction mixture is purified not by distillation but by chormatography on silica gel with hexane/ethyl acetate (9:1) as eluant.

$n_D^{20} = 1.4883$

Analysis: $C_{12}H_{22}OS$: Molecular weight: 214.4. Calc.: C, 67.3 %; H, 10.2 %; S, 15.0 %. Found: C, 66.4 %; H, 9.7 %; S, 15.0 %.

EXAMPLE 14

4-(4-Isopropoxy-2-butyloxy)-2-butanone 10 g (0.26 mol) of sodium borohydride are added at 20°–25°, over the course of 2 hours to 20 g (0.154 mol) of 4-isopropoxy-2-butanone, dissolved in 200 cc of ethanol. After a further 2 hours, the reaction mixture is concentrated by evaporation to 50 cc at reduced pressure, poured into 400 cc of water and the product extracted with ether. The ether solution is dried with sodium sulphate and evaporated. The residue is distilled at 35 mm, whereby 4-isopropoxy-2-butanol, having a B.P. of 88°/35 mm is obtained.

A mixture of 9.9 g (0.075 mol) of 4-isopropoxy-2-butanol and 7.0 g (0.1 mol) of methylvinyl is added dropwise at 20°–30° over the course of 30 minutes, to 3.3 g (0.025 mol) of 4-isopropoxy-2-butanol and 0.4 g of concentrated sulphuric acid. After stirring for 24 hours at 20°–25°, 0.7 g of potassium carbonate and 0.1 g of water are added. The reaction mixture is vigorously stirred at room temperature over the course of 3 hours, filtered and distilled. The resulting 4-(4-isopropoxy-2-butyloxy)-2-butanone has a B.P. of 75°–76°/1.0 mm.

$n_D^{20} = 1.4268$

Analysis: $C_{11}H_{22}O_3$: Molecular weight: 202.3. Calc. C, 65.3 %; H, 11.0 %. Found C, 65.0 %; H, 11.0 %.

EXAMPLE 15

4-(1-sec.Butoxy-3-pentyloxy)-2-butanone

The above compound is produced in analogous manner to that described in Example 14, but using 1-isopropoxy-3-pentanone in place of 4-isopropoxy-2-butanone. B.P. 95°–97°/1.2 mm. B.P.

$n_D^{20} = 1.4306$

Analysis: $C_{13}H_{26}O_3$: Molecular weight: 230.3. Calc.: C, 67.8 %; H, 11.4 %. Found: C, 67.8 %; H, 11.2 %.

EXAMPLE 16

7-Isopropoxy-5-methyl-4-heptenal 15.8 g (0.1 mol) of 5-isopropoxy-3-methyl-1-penten-3-ol and 20.0 g of mercuric acetate in 180 cc of ethyl vinyl ether are maintained at reflux temperature over the course of 4 days. 0.9 cc of glacial acetic acid is added at 20° to the turbid solution. After 3 hours 150 cc of 5 % potassium carbonate solution are added and the product is extracted with hexane. The hexane extract is dried with sodium sulphate and evaporated. The residue is heated to 165°–168° over the course of 1G2& hours without further purification and in an atomosphere of nitrogen; the residue is subsequently distilled at reduced pressure. The 7-isopropoxy-5-methyl-4-heptenal has a B.P. of 70°–73°/0.8 mm.

$n_D^{20} = 1.4476$

Analysis: $C_{11}H_{20}O_2$: Molecular weight: 184.3. Calc.: C, 71.7 %; H, 10.9 %. Found: C, 71.7 %; H, 10.8 %.

EXAMPLE 17

9-Isopropoxy-2-nonanone 1.4 g (0.015 mol) of solid potassium hydroxide are dissolved in 30 cc of 50 % aqueous methanol. 4.1 g (0.015 mol) of 3-carbethoxy-9-isopropoxy-2-nonanone are added to this solution and the mixture is heated to boiling temperature. After 1 hour at reflux the reaction mixture is cooled to 50°, neutralized with 50 % sulphuric acid, cooled to room temperature after 10 minutes, and 50 cc of water added. The product is extracted from the heterogeneous mixture with ether, the ether extract is washed with saturated salt solution, dried with sodium sulphate and evaporated. The residue is chromatographed on silica gel with hexane/ethyl acetate 9:1. Pure 9-isopropoxy-2-nonanone is obtained as a colourless oil.

$n_D^{20} = 1.4309$

Analysis: $C_{12}H_{24}O_2$: Molecular weight: 200.3. Calc.: C, 72.0 %; H, 12.1 %; O, 16.0 %. Found: C, 71.7 %; H, 11.9 %; O, 16.2 %.

EXAMPLE 18

8-Isopropoxy-6-methyl-2-octanone

The compound is produced in analogous manner to that described in Example 17, but using 3-carbethoxy-8-isopropoxy-6-methyl-2-octanone in place of 3-carbethoxy-9-isopropoxy-2-nonanone. B.P. 127°–129°/15 mm.

Analysis: $C_{12}H_{24}O_2$: MOlecular weight: 200.3. Calc. C, 72./ %; H, 12.1 %; O, 16.0 %. Found C, 71.3 %; H, 11.8 %; O, 17.3 %.

EXAMPLE 19

3-Carbethoxy-9-isopropoxy-2-nonanone 0.69 g (0.03 mol) of sodium are added at 20° to 20 cc of absolute ethanol. After complete reaction, 3.9 g (0.03 mol) of acetoacetic ester are added dropwise at 25° to the solution. The clear solution is then heated to 80° and, over a period of 1 hour, 6.7 g (0.03 mol) of 1-bromo-6-isopropoxy-hexane are added dropwise at reflux temperature. The turbid mixture is boiled at reflux for 16 hours and subsequently cooled to 20° and neutralized with alcoholic hydrochloric acid. After adding 20 cc of ether, the reaction mixture is filtered and the filtrate is evaporated. The residue is distilled, whereby, according to gas-chromatography, pure 3-carbethoxy-9-isopropoxy-2-nonanone, having a B.P. of 125°–130°/0.8 mm, is obtained.

Analysis: $C_{15}H_{28}O_4$: Molecular weight: 272.4. Calc.: C, 66.1 %; H, 10.4 %; O, 23.5 %. Found: C, 65.8 %; H, 10.4 %; O, 24.1 %.

EXAMPLE 20

3-Carbethoxy-8-isopropoxy-6-methyl-2-octanone

In manner analogous to that described in Example 19, the title compound may be produced, using 1-bromo-5-isopropoxy-3-methyl-pentane in place of 1-bromo-6-isopropoxy-hexane. B.P. 92°–94°/10⁻⁴ mm.

Analysis: $C_{15}H_{28}O_4$: Molecular weight: 272.4. Calc.: C, 66.1 %; H, 10.4 %; O, 23.5 %. Found: C, 66.1 %; H, 10.0 %; O, 23.9 %.

Compounds of formula XI

The following Examples 21 and 22 are representative of the process for producing compounds of formula XI:

EXAMPLE 21

1-Bromo-6-isopropoxy-hexane 1.15 g (0.05 mol) of finely cut sodium are added to 30 g (0.5 mol) of absolute isopropanol in an atmosphere of nitrogen; the mixture is stirred at 60° for 16 hours in order to dissolve the sodium completely. After cooling to 20°, 12.2 g (0.05 mol) of 1,6-dibromohexane are added and the mixture is stirred at reflux temperature for 18 hours. The precipitated sodium bromide is filtered off, the excess isopropanol is removed and the filtrate is distilled under vacuum. The main fraction (6.0 g), having a B.P. of 96°–98°/15 mm, is chromatographed on 300 g of silica gel with hexane/ethyl acetate (99:1), whereby 1-bromo-6-isopropoxy-hexane is obtained as a colourless oil.

Analysis: $C_9H_{19}BrO$: Molecular weight: 223.2. Calc.: C, 48.4 %; H, 8.5 %; Br, 35.8 %; O, 7.2 %. Found: C, 48.7 %; H, 8.4 %; Br, 35.9 %; O, 7.6 %.

EXAMPLE 22

1-Bromo-5-isopropoxy-3-methyl-pentane

A mixture of 16 g (0.1 mol) of 5-isopropoxy-3-methyl-1-pentanol and 2 g (/.25 mol) of pyridine is added dropwise at 0° to 10.9 g (0.04 mol) of phosphorous tribromide. The mixture is subsequently stirred at 25° for 2 hours and is then distilled at a bath temperature of 160°/12 mm into a receiver containing saturated sodium bicarbonate solution. (B.P. 100°–110°/12 mm).

The contents of the receiver are taken up with ether and successively washed with saturated sodium bicarbonate solution, 2N sulphuric acid, and saturated salt solution and dried with sodium sulphate. The ether is evaporated and the remaining 1-bromo-5-isopropoxy-3-methyl-pentane is purified by distillation. B.P. 90°–91°/12 mm.

Analysis: $C_9H_{19}BrO$: Molecular weight: 223.2. Calc.: C, 48.4 %; H, 8.6 %; Br, 35.8 %; O, 7.2 %. Found: C, 48.4 %; H, 7.9 %; Br, 35.6 %; O, 7.7 %.

The alcohols, used for the production of the compounds of formula XI, may be produced in accordance with known processes, e.g. as described in the following Example:

EXAMPLE 23

5-Isopropoxy-3-methyl-pentanol

A mixture of 34.4 g (0.261 mol) of 4-isopropoxy-2-butanol and 5.07 g (0.064 mol) of absolute pyridine is added dropwise at 0°C over the course of 15 minutes and while stirring to 28.4 g (0.105 mol) of phosphorous tribromide. After stirring for 2 hours at room temperature the reaction mixture is rapidly distilled in a vacuum B.P. 35°–60°/12 mm. The distillate is taken up in ether, successively washed with ice cold dilute sodium bicarbonate solution, water, ice cold 2N sulphuric acid, water and then saturated sodium chloride solution, dried over sodium sulphate and separated from the ether by fractional distillation.

The residue is fractionally distilled and 2-bromo-4-isopropoxy-butane, having a B.P. of 69°–70°/24 mm, is obtained.

To an ethanolic sodium ethanolate solution, produced from 9.45 g of sodium and 200 cc of absolute ethanol, is added, in an atomsophere of nitrogen at 50°C over a peroid of 15 minutes while stirring, 67.7 g (0.423 mol) of diethyl-malonate, and subsequently 80.0 g (0.410 mol) of 2-bromo-4-isopropoxy-butane over a further period of 15 minutes. The mixture is boiled at reflux for 24 hours, then neutraliued with glacial acetic acid and separated from the main amount of ethanol by distillation.

The residue is treated with ice-water, and extracted with ether. The ether extract is washed with water and saturated salt solution, dried over sodium sulphate and the ether evaporated off in a vacuum. The resulting crude ethyl-[2-carbethoxy-5-isopropoxy-3-methyl]-n-pentanoate may be reacted without additional purification.

110 g of crude ester are added dropwise at 60° over a period of 15 minutes and while stirring to 180 g of 50 % KOH (1.60 mol) and the mixture is boiled at reflux for 2 hours. After adding 100 cc of water the ethanol produced by hydrolysis is distilled off at normal pressure. The residue, acidified with 250 cc of 6N sulphuric acid at 10°C while stirring is extracted with ether, the ether extract is washed with a small amount of water and saturated sodium chloride, dried over sodium sulphate and evaporated. The remaining crude dicarbonic acid is decarboxylated by stirring at 190°C for 1 hour and the product is subsequently distilled in a vacuum. 5-Isopropoxy-3-methyl-n-pentanoic acid, having a B.P. of 89°–91°C/0.1 mm, is obtained.

Analysis: $C_9H_{18}O_3$: Molecular weight: 174.2. Calc.: C, 62.0 %; H, 10.4 %; O, 27.5 %. Found: C, 62.0 %. H, 10.4 %; O, 27.6 %.

A solution of 19.8 g (0.114 mol) of 5-isopropoxy-3-methyl-n-pentanoic acid in 120 cc of absolute benzene is added dropwise over a period of 1 hour to 96 cc (0.342 mol) of 70 % sodium-bis-(2-methoxy-ethoxy)-aluminium-dihydride in 220 cc of absolute benzene. The mixture is boiled at reflux for 2 hours, cooled to 10°C, acidified with 2N sulphuric acid while stirring and is extracted with ether. The ether extract is washed with a small amount of water and saturated sodium chloride solution, dried over sodium sulphate and the ether evaporated off.

The residue is chromatographed with hexane: ethyl acetate (9:1) on 600 g of silica gel and 5-isopropoxy-3-methyl-pentanol is obtained as colourless oil.

Analysis: $C_9H_{20}O_2$: Molecular weight: 160.3. Calc.: C, 67.5 %; H, 12.6 %; O, 20.0 %. Found: C, 67.3 %; H, 12.7 %; O, 20.2 %.

The halide stage which is employed in the production of the Grignard compounds of formula V, employed in the production of compounds of formula I in accordance with process c), may, for example, be produced in accordance with the following Example:

EXAMPLE 24

1-Bromo-6-isopropoxy-4-methyl-3-hexene

To the Grignard reagent [production according to E. Renk et al. J. Am. Chem. Soc. 83, 1987 (1961)], from 9.06 g (0.37 mol) of magnesium and 42.8 g (0.35 mol) of cyclopropyl bromide in 460 cc of absolute tetrahydrofurane, is added dropwise at 5°C over the course of 10 minutes, in an atomosphere of nitrogen and while stirring, a solution of 46 g (0.35 mol) of 4-isopropoxy-2-butanone in 100 cc of absolute tetrahydrofurane. After stirring the reaction mixture at room temperature for 20 hours, saturated ammonium chloride solution and ice are added and the mixture is extracted with ether. The ether extract is washed with saturated salt solution, dried over sodium sulphate and the ether evaporated off. The resulting 2-cyclopropyl-4-isopropoxy-2-butanol is obtained after distillation at 75°–79°/12 mm as a colourless oil.

19 cc of 48 % hydrobomic acid are added dropwise at 0°C over a period of 15 minutes and while stirring, to 27.7. g of 2-cyclopropyl-4-isopropoxy-2-butanol [Method of M. Julia et al, Bull, Soc. Chim. France 1072 (1960)]. The mixture is stirred at 0°–5° for 30 minutes and is subsequently extracted with ether. The ether extract is washed with water, saturated sodium bicarbonate solution, and saturated salt solution, dried over sodium sulphate and the ether evaporated off.

The residue is chromatographed with hexane/ethyl acetate (98:2 and 95:5) on silica gel. The chromatographically pure mixture of the cis-trans isomers of 1-bromo-6-isopropoxy-4-methyl-3-hexene is obtained as colourless oil.

$n_D^{20} = 1.4802$

Analysis: $C_{10}H_{19}BrO$: Molecular weight: 235.2. Calc.: C, 51.1 %; H, 8.1 %; Br, 34.0 %. Found: C, 51.1 %; H, 8.3 %; Br, 33.2 %.

Compounds of formula XII

The following Examples 25 and 26 are representative of the process for producing the ketones of formula XII, wherein $R_2$ signifies a lower alkyl group of 1 to 4 carbon atoms.

EXAMPLE 25

5-Isopropoxy-2-butanone 0.3 g of concentrated sulphuric acid is added to 7.2 g (0.12 mol) of isopropanol. A mixture of 21 g (0.33 mol) of vinyl methyl ketone and 36 g (0.6 mol) of isopropanol is added dropwise at room temperature over a period of 1 hour and while stirring, the temperature not exceeding 30°. After 24 hours 1.6 g of potassium carbonate amd 2 drops of water are added at room temperature, the mixture is vigorously stirred for 2 hours, is filtered and the clear neutral filtrate is fractionated at 36 mm. The excess of isopropanol is first distilled off and then the 4-isopropoxy-2-butanone distills over at 73°–76°/36 mm.

EXAMPLE 26

4-Isopropylthio-2-butanone

The above compound is produced in analogous manner to that described in Example 24, but using isopropyl mercaptan in the place of isopropanol. B.P. 94°–96°/17 mm.

Compounds of formula VIII

The following Examples are representative of the process for producing the alcohols of formula VIII.

EXAMPLE 27

5-Isopropoxy-3-methyl-1-penten-3-ol 12 g (0.5 mol) of magnesium turnings are covered wtih a layer of 60 cc of absolute tetrahydrofurane in an atmosphere of nitrogen in a flask equipped with a stirrer and a reflux condenser and heated to 40°–45°. 5 cc of a solution of 53.5 g (0.5 mol) of vinyl bromide in 100 cc of absolute tetrahydrofurane are added dropwise by means of a dropping funnel, whereupon an exothermic reaction commences. The remaining vinyl bromide solution is added dropwise at such rate that the reaction mixture is maintained at a temperature of 45°–50° (approximately 1 to 1 1/2 hours). The mixture is then stirred at 50° for 1 hour and is subsequently cooled to 0°. 52 g (0.4 mol) of 4-isopropoxy-2-butanone in 100 cc of absolute tetrahydrofurane are added dropwise over a period, of 45 minutes and while stirring vigorously and the reaction mixture is subsequently stirred at room temperature over a period of 16 hours. After this period 250 cc of 20 % ammonium chloride solution are added over a period of 15 minutes to the reaction mixture which is cooled to 50°–10°. The mixture is stirred for 15 minutes and is extracted with ether. The ether extract is washed with water in a separating funnel, dried with sodium sulphate and evaporated. The residue is fractionated at a pressure of 13 mm, whereby the 5-isopropoxy-3-methyl-1-penten-3ol distills over at 72°-73°.

$n_D^{20} = 1.4297$

Analysis: $C_9H_{18}O_2$: Molecular weight: 158.2. Calc.: C, 68.3 %; H, 11.5 %. Found: C, 68.1 %; H, 11.4 %.

EXAMPLE 28

5-Isopropylthio-3-methyl-1-penten-3-ol

The above compound is produced in analogous manner to that described in Example 27, but using 4-isopropylthio-2-butanone in place of 4-isopropoxy-2-butanone. B.P. 79°-80°/1.2 mm.

$n_D^{20} = 1.4813$

Analysis: $C_9H_{18}OS$: Molecular weight: 174.3. Calc.: C, 62.5 %; H, 10.4 %; S, 18.4 % Found: C, 61.5 %; H, 10.4 %; S, 18.9 %.

What is claimed is:

1. A compound of the formula:

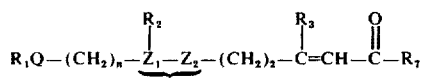

wherein $R_1$ is alkyl of 1 to 10 carbon atoms; alkenyl of 3 to 10 carbon atoms; alkynyl of 3 to 10 carbon atoms; cycloalkyl of 3 to 6 carbon atoms; cycloalkyl of 3 to 6 carbon atoms substituted by alkyl of 1 to 4 carbon atoms; cycloalkenyl of 5 to 7 carbon atoms; cycloalkenyl of 5 to 7 carbon atoms substituted by alkyl of 1 to 4 carbon atoms; cycloalkyl (of 3 to 6 carbon atoms)alkyl (of 1 to 4 carbon atoms); cycloalkyl(of 3 to 6 carbon atoms)alkyl (of 1 to 4 carbon atoms) ring substituted by alkyl of 1 to 4 carbon atoms; cycloalkenyl(of 5 to 7 carbon atoms)alkyl (of 1 to 4 carbon atoms); or cycloalkenyl (of 5 to 7 carbon atoms) alkyl (of 1 to 4 carbon atoms) ring substituted by alkyl of 1 to 4 carbon atoms;

$R_2$ and $R_3$, which are the same or different are each hydrogen or alkyl of 1 to 4 carbon atoms, $R_7$ is alkyl of 1 to 5 carbon atoms;

Q is oxygen or sulphur;

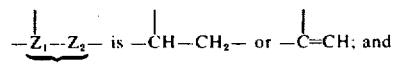

$n$ is an integer 1, 2 or 3.

2. A compound of claim 1 of the formula:

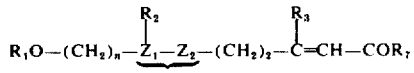

wherein $R_1$ is alkyl of 1 to 6 carbon atoms, $R_2$ and $R_3$ mare independently hydrogen or alkyl of 1 to 4 carbon atoms,

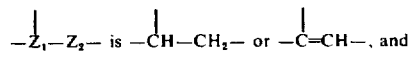

$n$ is 1 to 3.

3. A compound of claim 2, in which $R_1$ is isopropyl or sec.butyl, in which $R_2$ is hydrogen, methyl or ethyl, $R_3$ is hydrogen or methyl and $n$ is 2 or 3.

4. The compound of claim 1, which is 10-isopropoxy-8-methyl-3,7-decadien-2-one.

5. The compound of claim 1, which is 10-isopropoxy-4,8-dimethyl-3,7-decadien-2-one.

* * * * *